(12) United States Patent
Matsuda et al.

(10) Patent No.: US 7,147,825 B2
(45) Date of Patent: Dec. 12, 2006

(54) MEASURING SYSTEM

(75) Inventors: Kouichi Matsuda, Ehime (JP);
Masashi Watanabe, Ehime (JP);
Yoshiharu Sato, Kyoto (JP); Etsuo Hirao, Kyoto (JP)

(73) Assignees: Matsushita Electric Industrial Co., Ltd., Osaka (JP); Arkray, Inc., Kyoto (JP)

( * ) Notice: Subject to any disclaimer, the term of this patent is extended or adjusted under 35 U.S.C. 154(b) by 435 days.

(21) Appl. No.: 09/958,888

(22) PCT Filed: Feb. 19, 2001

(86) PCT No.: PCT/JP01/01151

§ 371 (c)(1),
(2), (4) Date: Dec. 19, 2001

(87) PCT Pub. No.: WO01/61341

PCT Pub. Date: Aug. 23, 2001

(65) Prior Publication Data

US 2002/0155030 A1    Oct. 24, 2002

(30) Foreign Application Priority Data

Feb. 18, 2000  (JP) ............................. 2000-041714

(51) Int. Cl.
*G01N 33/48* (2006.01)
(52) U.S. Cl. .................... 422/58; 422/56; 422/61; 436/164; 436/169
(58) Field of Classification Search ............... 422/58, 422/61, 164, 169, 56; 436/66
See application file for complete search history.

(56) References Cited

U.S. PATENT DOCUMENTS

| 5,597,532 | A | * | 1/1997 | Connolly ................... 422/58 |
| 5,786,584 | A | * | 7/1998 | Button et al. .......... 235/462.15 |
| 5,872,713 | A | | 2/1999 | Douglas et al. |
| 6,045,756 | A | * | 4/2000 | Carr et al. ............... 422/82.11 |
| 6,106,780 | A | * | 8/2000 | Douglas et al. ............... 422/58 |

FOREIGN PATENT DOCUMENTS

| AU | 9851575 | 5/1998 |
| DE | 29723400 | 9/1998 |
| DE | 19781162 | 3/1999 |
| DE | 29723665 | 3/1999 |
| GB | 2322444 | 8/1998 |
| JP | 62-3649 | 1/1987 |
| JP | 62003649 | 1/1987 |
| JP | 11-510915 | 9/1999 |
| WO | 98/19159 | 7/1998 |

* cited by examiner

*Primary Examiner*—Lyle A. Alexander
(74) *Attorney, Agent, or Firm*—Wenderoth, Lind & Ponack, L.L.P.

(57) ABSTRACT

A measuring system according to the present invention includes a biosensor 29, a measuring device 54 for assaying a specified component in a biological sample applied to the sensor 29, optional indicating equipment 56 which can be removed from the measuring device 54 and announces a measurement result by the measuring device 54 or the like by voice, and a guide 50 for guiding a target to be measured to the sensor 29. According to this measuring system, it is possible to remove the difficulty of performing locating operations when a blind person or a person having weak eyesight attaches/detached the sensor 29 to/from a connector 13 of the measuring device 54 or applies body fluid such as blood to the end of the sensor 29.

25 Claims, 5 Drawing Sheets

MEASURING SYSTEM

TECHNICAL FIELD

The present invention relates to a measuring system suitable for a biosensor which can accurately, speedily, and easily assay a specific component in various types of a biological sample and, more particularly, to a measuring system which is surely handled by a blind person or a person having weak eyesight.

BACKGROUND ART

In recent years, various types of biosensors which utilize a specific catalytic action by an enzyme have been developed, and attempts have been made to apply these biosensors to a clinical field. A biosensor which can speedily and accurately perform measurement is desired.

When a glucose sensor is cited as an example, conventionally, a patient measures plasma by centrifuging blood in order to measure and manage a blood sugar level, which results in considerably complicated procedures. Therefore, a sensor which enables measurement of whole blood is desired in these days of rapid increase in the number of diabetic patients.

There is a simplified form, in which a stick-type support body is provided with a carrier including an enzyme that reacts only to sugar (glucose) and a color matter which is changed during an enzyme reaction or by a product of the enzyme reaction, similar to examination paper used during a urine examination. This is a method in which blood is dropped on the carrier to visually or optically measure the change of the color matter after a certain period of time. However, according to this method, accuracy becomes low due to large interference by a coloring substance in the blood.

On the other hand, a measuring system which is disposable with an electrode system at every measurement has also been proposed. While the measuring operation is considerably simplified, such a measuring device system becomes very expensive in view of an electrode material such as platinum and the like, or the construction. While a sputtering method or a deposition method can be employed as a manufacturing method of platinum electrodes, the manufacturing cost is very high.

A biosensor disclosed in Japanese Published Patent Application No. Sho. 61-294351 is proposed as a method which makes the measuring device disposable with an electrode system. According to these measurements, prescribed voltage is applied to an electrode system of the sensor to measure a value of an electric current flowing between electrodes, and concentration of a substrate in a sample liquid is calculated based on the signal. Conventionally, as illustrated in FIG. 7, aluminum package material 40 for packing a sensor 29 is opened to a prescribed position, and the sensor is inserted to a connector part of a measuring device 54, which holds the sensor pinched by the aluminum package 40. Then, after conforming by a display means 30 that the power is automatically turned on, blood is applied to the edge of the sensor 29, thereby performing a measurement.

According to a measuring system having the conventional construction, a connector part of the measuring device is small and its position is hard to be found, so that it is difficult to determine a position to insert the sensor to the connector part of the measuring device or to apply blood of a fingertip or the like to a prescribed position of the sensor. Particularly, the handling is considerably difficult for a blind person or a person having weak eyesight.

The present invention is made to solve the above-mentioned problems. In particular, its object is to provide a measuring system in which an insert position of a sensor and an applying position of blood or the like in a measuring device are easy to be found by attaching a guide for a fingertip. Thus, a specified component in a biological sample such as blood can be easily, speedily, and accurately measured.

SUMMARY OF THE INVENTION

According to the present invention, there is provided a measuring system comprising a sensor and a measuring device for assaying a specified component in a biological sample applied to the sensor. A new sensor is mounted to the measuring device every time a property of a target to be measured is measured, so as to perform a measurement. The system includes a guide for guiding the target to be measured to the sensor. Therefore, a user such as an elderly person or a person having weak sight can easily perform a measuring operation of a target to be measured, resulting in easy handling of the system.

According to the present invention, in the measuring system as described above, the guide is provided at the forward side of the measurement part of the sensor. Therefore, a user such as a weak-sighted or elderly person performs a sliding operation of his/her finger along the guide holding the measuring device, thereby easily applying a target to be measured to the side of the sensor.

According to the present invention, in the measuring system as described above, the guide can be pulled out of or stored in the measuring device. Therefore, a user such as a person having weak sight or an elderly person can easily operate the system, thereby easily performing a measuring operation without any troublesome operations for each measurement.

According to the present invention, a measuring system comprises a sensor, a measuring device for assaying a specified component in a biological sample applied to the sensor, and optional equipment which announces a measurement result by the measuring device or the like by voice. A new sensor is mounted to the measuring device every time a property of a target to be measured is measured, so as to perform a measurement, and a guide for guiding the target to be measured to the sensor is attached to the side of the optional equipment. Therefore, a user such as a person having weak sight or an elderly person who needs to use the optional equipment can easily operate the system and apply a target to be measured to the sensor.

According to the present invention, in the measuring system as described above, the guide is employed as a clamp for fixing the measuring device with the optional equipment. Therefore, a complicated mechanism is not especially required, whereby a user such as a person having weak sight or an elderly person can easily perform a measuring operation without any bothersome operations at every measurement.

According to the present invention, in the measuring system as described above, the guide can be pulled out of or stored in the optional equipment. Therefore, a complicated mechanism is not especially required, so that a user such as a person having weak sight or an elderly person can easily perform a measuring operation without any bothersome operations at every measurement.

According to the present invention, in the measuring system as described above, the guide is V-shaped so as to guide a fingertip to the sensor to which the target to be measured is applied. Therefore, a user such as a person having weak sight or an elderly person can easily find the guide position and can perform a sliding operation of his/her finger along the guide, thereby easily applying a target to be measured to the sensor.

According the present invention, in the measuring system as described above, the guide is made of a material having a spring elasticity. Therefore, even a person having weak sight or an elderly person can easily perform handling of the guide as a clamp.

According to the present invention, in the measuring system as described above, the guide has a groove formed from the end of the measuring device. Therefore, a user such as a person having weak sight or an elderly person can perform a sliding operation of his/her finger along the guide, thereby easily applying a target to be measured to the sensor.

According to the present invention, in the measuring system as described above, the guide pushes the end or top surface of the measuring device. Therefore, a complicated mechanism is not especially required, so that a user such as a person having weak sight or an elderly person can easily perform a measuring operation without any bothersome operations at every measurement.

According to the present invention, in the measuring system as described above, the guide is removable from the optional equipment. Therefore, the guide can be easily removed when not needed.

DETAILED DESCRIPTION OF THE INVENTION

Hereinafter, a measuring system according to the present invention will be described on the basis of a concrete embodiment.

Figure 1:
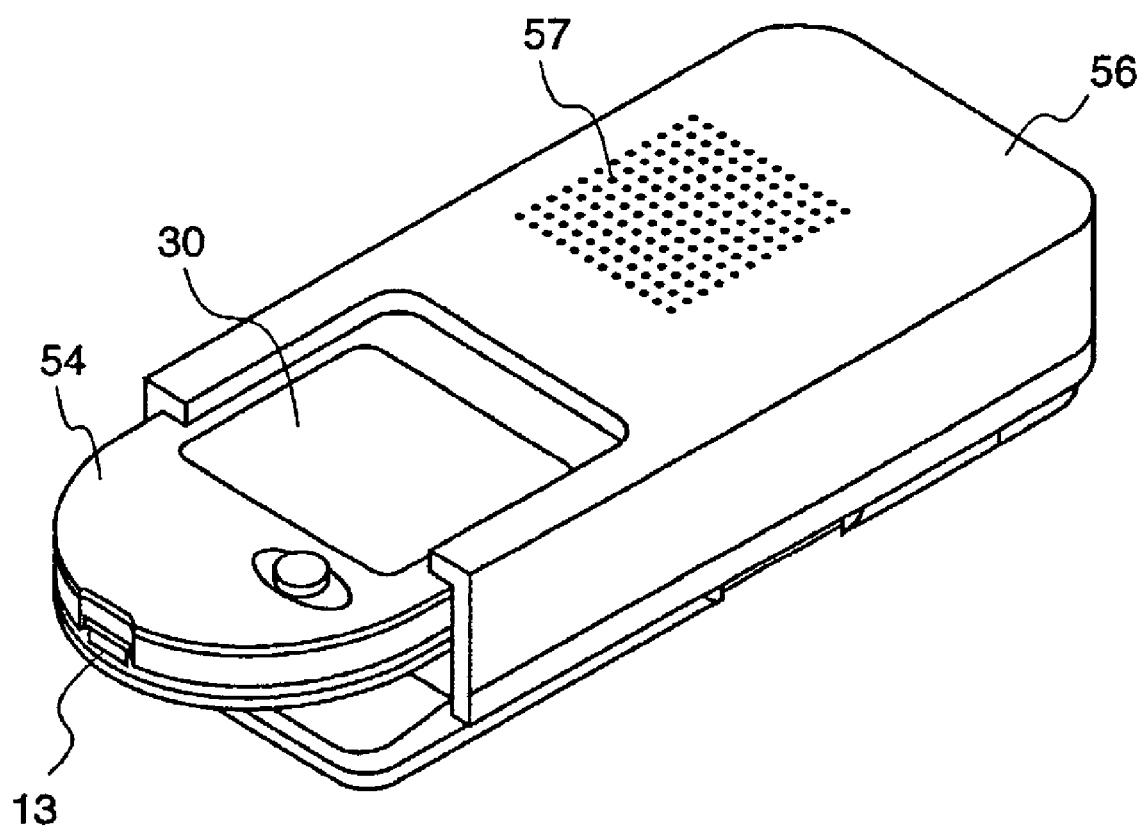
FIG. 1 is a perspective view of a measuring system according to an embodiment of the present invention.
Figure 2:
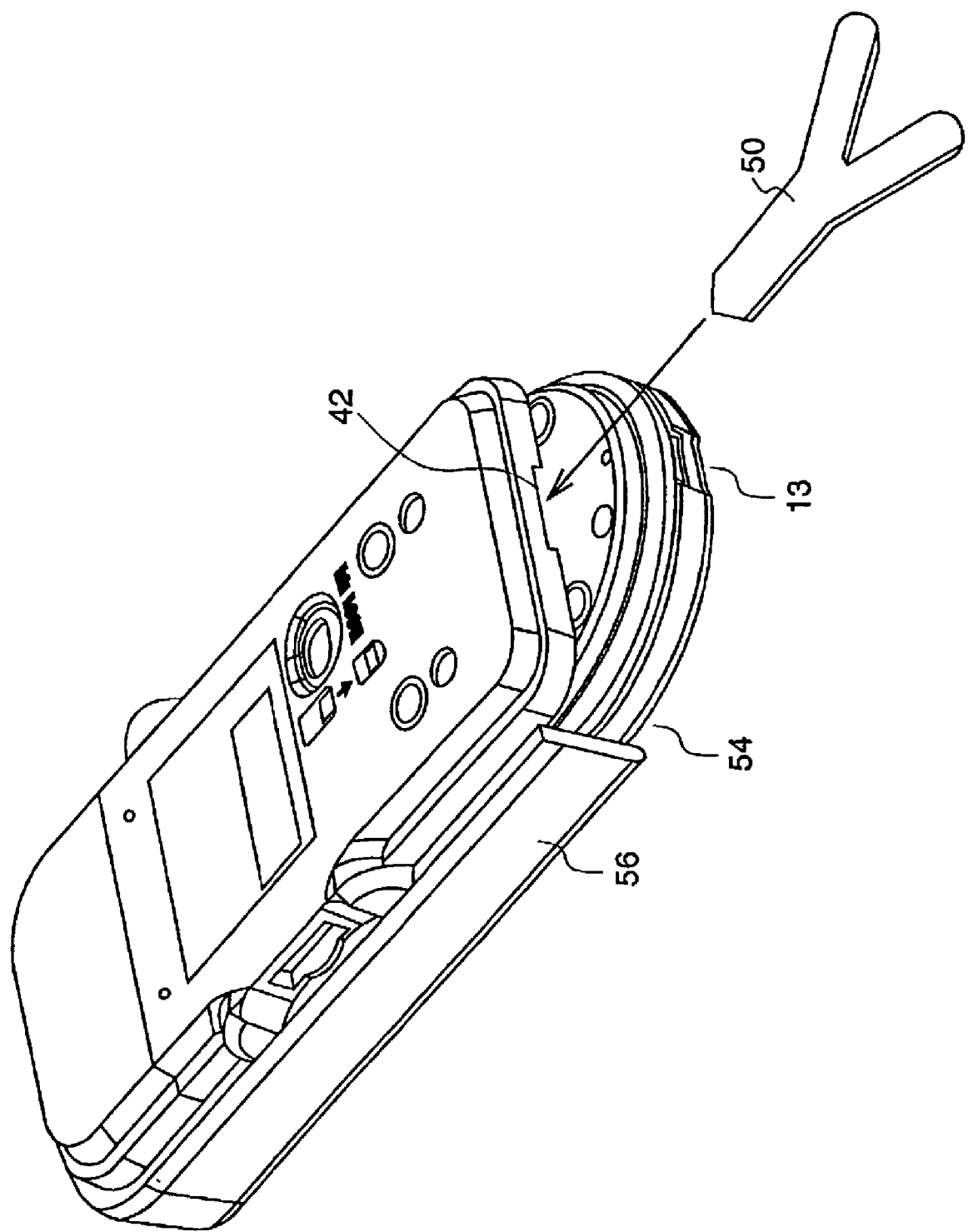
FIG. 2 is a perspective view of the measuring system seen from the bottom side according to the embodiment of the invention.
Figure 3:
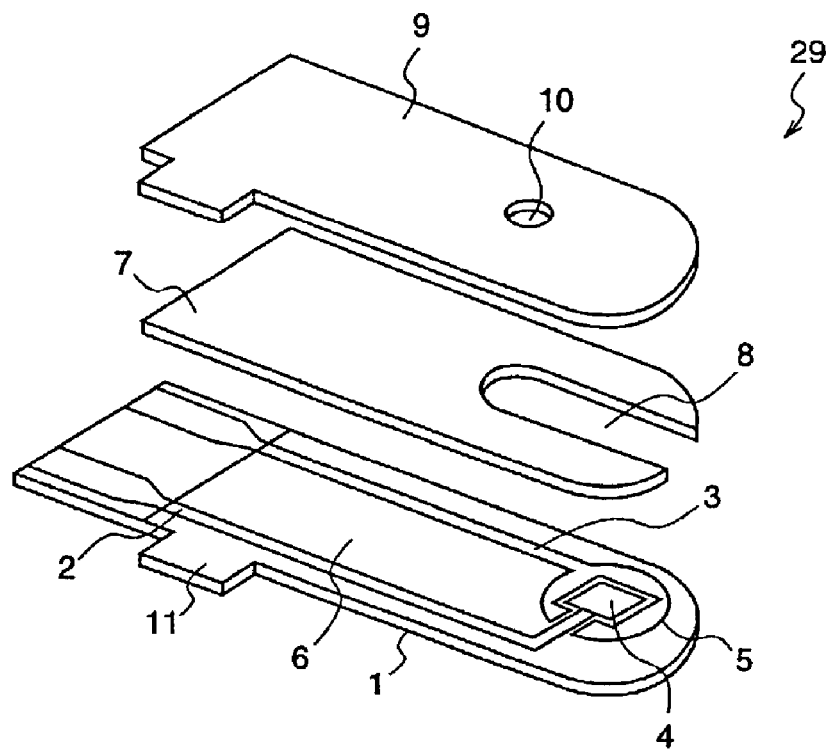
FIG. 3 is an exploded perspective view of a biosensor used for the measuring system according to the embodiment of the invention.

FIG. 1 is an external perspective view of the measuring system, FIG. 2 is a perspective view of the measuring system seen from the bottom side, and FIG. 3 is an exploded perspective view of a biosensor (hereinafter, abbreviated to sensor).

As shown in FIG. 1, in a state in which a measuring device 54 is united with optional indicator equipment 56, a sensor 29 shown in FIG. 3 is inserted in a connector 13, and liquid to be examined (such as blood) is applied to the end of the sensor 29. Thus, a measurement result in the measuring device 54 is sent to the optional indicator equipment 56, which announces the measurement result by voice from a voice output means 57 of the optional indicator device 56. A new sensor 29 is mounted to the measuring device 54 each time a target is to be measured. In other words, the sensor 29 is detachable from the measuring device and replaceable.

Further, a counter electrode 5, a measuring electrode 4, leads 3 and 2 connected thereto, and an insulating layer 6 are provided on a substrate 1 of the sensor 29 as shown in FIG. 3. A reactive layer, which is not shown, which includes an enzyme and a mediator (electron acceptor) is formed as if the counter electrode 5 and the measuring electrode 4 are covered therewith. A cover 9 is fixed on the substrate 1 through the intermediary of a spacer 7. Numeral 8 denotes a sample supply opening, through which liquid to be examined (sample) is introduced onto the counter electrode 5 and the measuring electrode 4 by capillary action. The air inside is discharged from an air vent 10 together with the introduction of the liquid to be examined. Numeral 11 denotes a projection for preventing an inverse insertion, by which a reverse insertion to the body of the measuring device 54 can be prevented. A usage example of a guide in the measuring device according to the invention will be described with reference to FIGS. 2, 4, and 5.

Figure 4:
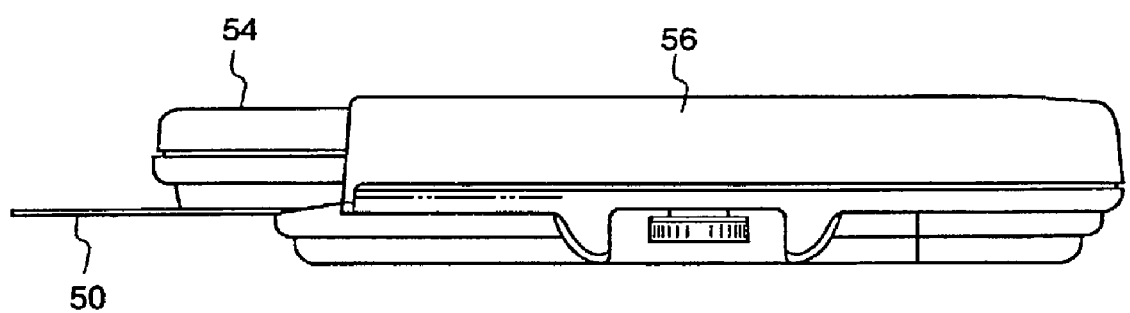
FIG. 4 is a side view illustrating a state where a guide is attached to optional equipment in the measuring device according to the embodiment of the invention.
Figure 5:
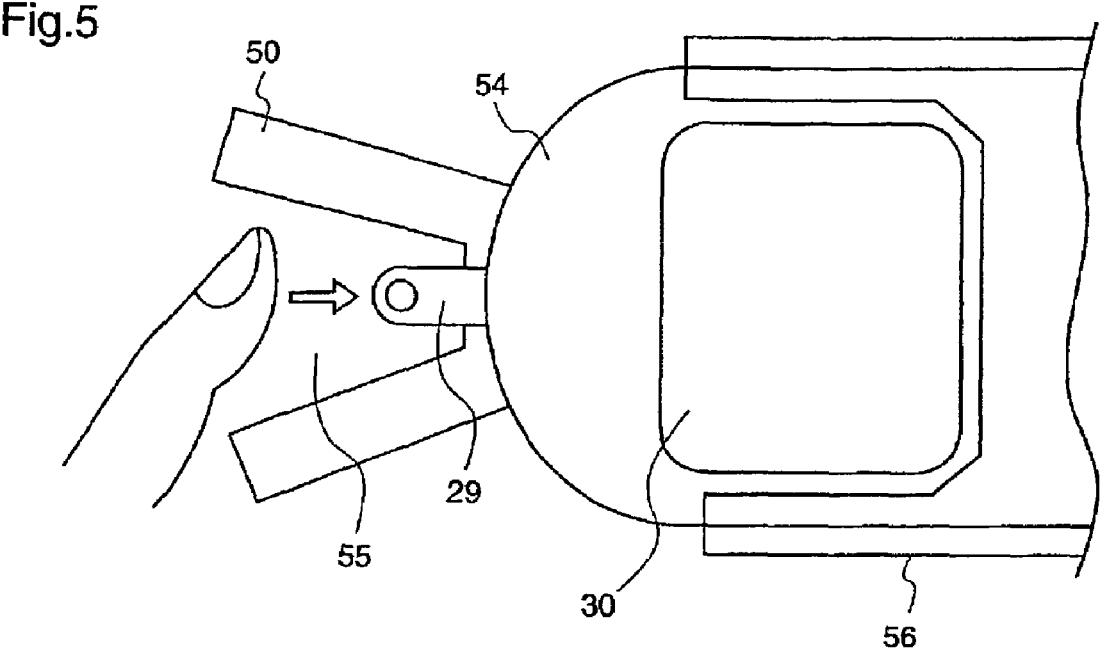
FIG. 5 is a plan view of a measuring system exemplifying use of the guide of the measuring system according to the embodiment of the invention.

FIG. 4 is a side view of the measuring system. FIG. 5 is a plan view illustrating a sectional construction of a guide 50 for applying body fluid to the sensor and a sensor hold part in the measuring system. As illustrated in FIGS. 2, 5, 6(*a*), and 6(*b*), the guide 50 has a pair of guide arms that project outwardly from the sensor 29 so that the sensor 29 is located between the guide arms (see FIG. 5). The guide arms are connected to a base portion as shown in FIG. 2, and the base portion is connected to the indicator device 56 (see FIGS. 6(*a*) and 6(*b*), or to the measuring device 54.

As shown in FIG. 2, in a state in which the optional equipment 56 is attached to the measuring device 54, the base portion of the guide 50 is inserted into a guide insertion slot 42 of the optional equipment 56, and the sensor 29 is inserted into the connector 13 of the measuring device 54, so that the guide 50 can be employed as a guiding means for a fingertip. After completing a puncture of a fingertip by a lancet, a measurement operator moves his/her fingertip to the end of the sensor 29 along a guiding groove 55 for guiding a fingertip, which is provided in the guide 50, so as to perform an applying operation of prescribed body fluid, as shown in FIG. 5. While the guide is V-shape in the embodiment, it may have any shape other than the V-shape as long as there is a groove which leads a fingertip to the end of the measuring device where the sensor is attached.

Thereafter, at the end of the sensor 29 to which body fluid is applied, a prescribed measurement result concerning the body fluid is indicated by voice or pressure by optional indicator equipment 56, or by a display 30 such as an LCD of the measuring device 54 due to progress of an enzyme reaction.

When this measuring operation is completed, the measurement operator confirms the position of the sensor 29 using the guide 50 as a mark, and concludes the operation by taking the sensor 29 out of the connector 31.

Figure 6A:
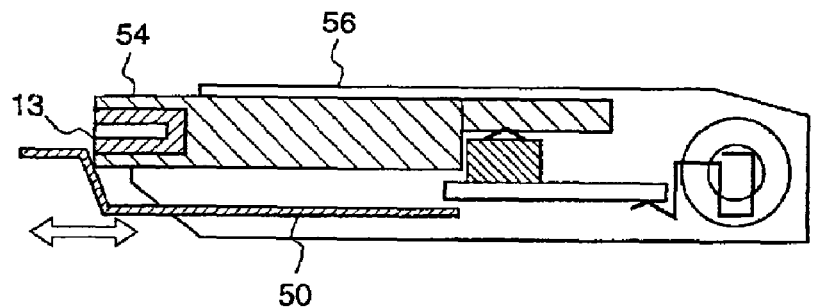
FIG. 6 is a sectional view of a measuring system according to another embodiment of the present invention.
Figure 6B:
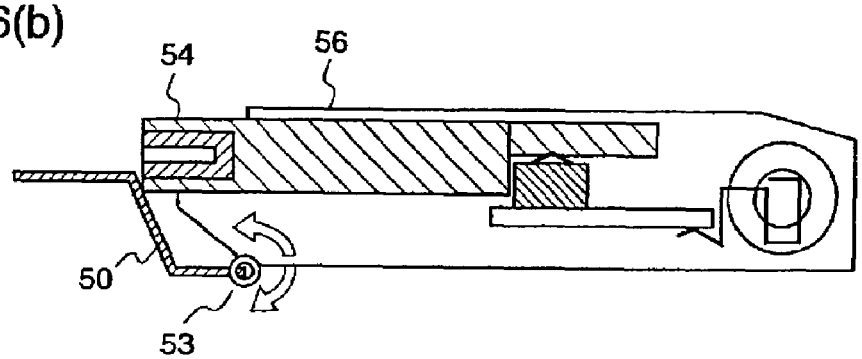
Figure 7:
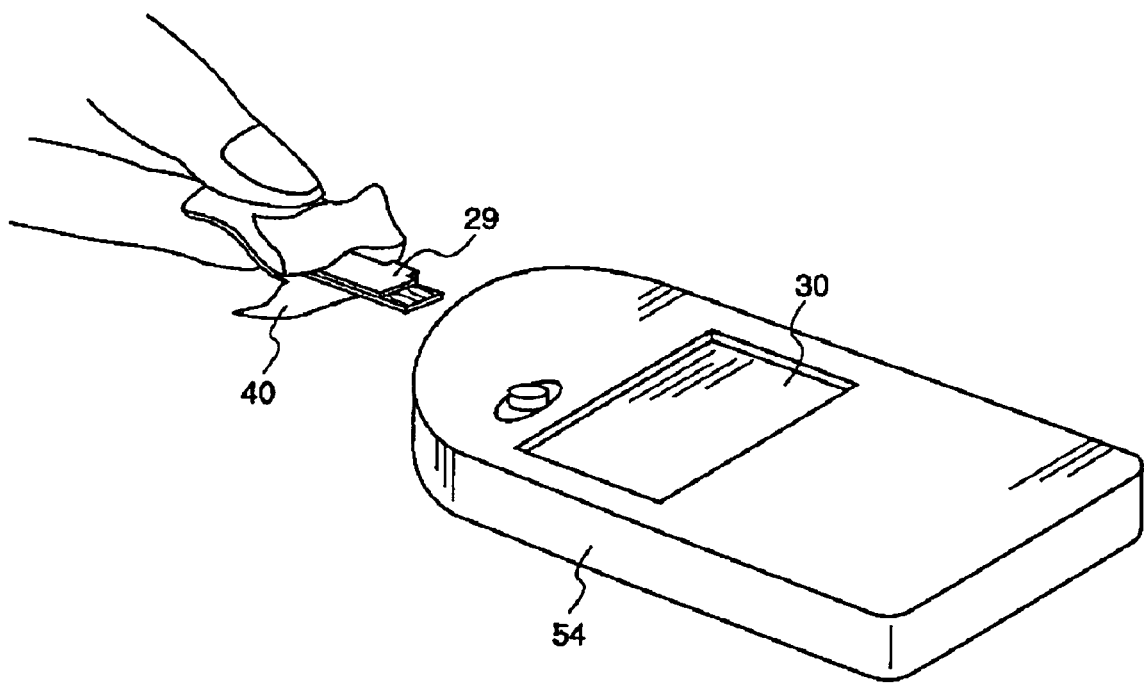
FIG. 7 is a perspective view of a conventional measuring device.

Here, the guide 50 is attached to the optional indicator equipment 56 which is attached to the measuring device 54 in a case of usage by a blind person, a person having weak eyesight or an elderly person, or is inserted into a fitting part of the measuring device 54 and the optional equipment 56. In a case in which the guide 50 is inserted into the fitting part, the guide 50 is conformed as shown in above-described FIG. 4. On the other hand, in a case in which the guide 50 is attached to the side of the optional indicator equipment 56, the guide 50 can be used as a clamp for fixing the measuring device 54 and the optional indicator equipment 56, as shown in FIGS. 6(a) and (b). In FIG. 6(a), the guide 50 is stored in the optional indicator equipment 56 and can move in an arrow direction due to a sliding system (i.e., is retractably attached), which results in a compact shape. In FIG. 6(b), the guide 50 can be constructed to rotate around a supporting point 53 of the optional indicator equipment 56. In either case, the end of the guide 50 is inflected (i.e., bent), thereby to obtain a clampable shape at the end of the measuring device 54.

As a material of the guide 50, a material especially having a spring elasticity (such as SUS material or Duracon) is employed, so that the guide can be employed as a stronger clamp due to its own spring elasticity.

As described in the above-mentioned embodiment, when the guide 50 is employed, it is possible to remove the difficulty of locating operations when a blind person or a person having weak eyesight attaches/detaches the sensor 29 to/from the measuring device 54, or applies body fluid such as blood of a fingertip to the end of the sensor 29, thereby reducing trouble or labors operations during usage. Further, the mechanism for guiding a target to be measured to the sensor 29 can be realized by a simple construction such as the guide 50.

In the above description, as the sensor 29, a type of sensor which utilizes capillary action as a method of leading blood to an enzyme electrode part is described. However, even when a sensor which drops blood directly to the enzyme electrode part is employed, the same effects can be obtained.

Further, the guide 50 may be constructed to be attached to the measuring electrode 54 directly, in addition to the construction as described in the above-mentioned embodiments. For example, the guide 50 may be detachable from the measuring device 54, or may have a construction similar to that shown in FIG. 6, in which the guide 50 is stored in the measuring device 54 by a sliding system, or may be supported to rotate freely.

APPLICABILITY IN INDUSTRY

As described above, a measuring system according to the present invention can remove the difficulty of performing locating operations when a sensor is attached/detached to/from a measuring device, or when body fluid such as blood of a fingertip is applied to the end of the sensors. More particularly, the measuring system can be used by a blind person or a person having weak eyesight with a in reduction of trouble or labor operation during the usage.

The invention claimed is:

1. A measuring system comprising:
a sensor for sensing a specified component in a biological sample;
a measuring device for assaying the specified component sensed by said sensor, said sensor being detachably connected to said measuring device so as to project outwardly from said measuring device in a projecting direction; and
a V-shaped guide having a pair of guide pieces each projecting outwardly from said measuring device farther than an end portion of said sensor in a respective outward direction relative to the projecting direction of said sensor, said pair of guide pieces being arranged to define a space therebetween, said space extending outwardly from said measuring device in the projecting direction of said sensor such that said end portion of said sensor is located within said space when said sensor is connected to said measuring device and such that said pair of guide pieces guide a target toward said sensor.

2. The measuring system of claim 1, wherein said pair of guide pieces comprises a pair of guide arms projecting outwardly at opposite sides of said sensor.

3. The measuring system of claim 2, wherein said guide further has a base portion attached to said measuring device, said guide arms projecting outwardly from said base portion of said guide, said sensor being attached to said measuring device.

4. The measuring system of claim 1, wherein said pair of guide pieces comprises a pair of guide arms projecting outwardly from said measuring device so that a tip portion of each of said guide arms is located farther from said measuring device than said end portion of said sensor with respect to the projecting direction.

5. The measuring system of claim 4, wherein said guide further has a base portion attached to said measuring device, said guide arms projecting outwardly from said base portion of said guide, said sensor being attached to said measuring device.

6. The measuring system of claim 1, wherein said sensor projects from a front side of said measuring device, said guide being attached to said measuring device such that said pair of guide pieces project from said front side of said measuring device at opposite sides of said sensor.

7. The measuring system of claim 1, wherein said sensor comprises a disposable sensor detachably connected to said measuring device.

8. The measuring system of claim 1, wherein said guide projects outwardly from a measurement portion of said sensor so as to guide the target toward said measurement portion of said sensor.

9. The measuring system of claim 1, wherein said guide is retractably attached to said measuring device so as to be pulled from and stored in said measuring device.

10. The measuring system of claim 1, wherein said space defined by said pair of guide pieces of said V-shaped guide comprises a guiding groove extending from an open end of said guide toward said sensor.

11. The measuring system of claim 1, wherein said guide is made of a material having a spring elasticity.

12. A measuring system comprising:
a sensor for sensing a specified component in a biological sample;
a measuring device for assaying the specified component sensed by said sensor, said sensor being detachably connected to said measuring device so as to project outwardly from said measuring device in a projecting direction;
an indicator device for indicating a measured result generated by said measuring device; and
a V-shaped guide having a pair of guide pieces each projecting outwardly from said measuring device farther than an end portion of said sensor in a respective outward direction relative to the projecting direction of said sensor, said pair of guide pieces being arranged to define a space therebetween, said space extending outwardly from said measuring device in the projecting direction of said sensor such that said end portion of said sensor is located within said space when said sensor is connected to said measuring device and such that said pair of guide pieces guide a target toward said sensor.

13. The measuring system of claim 12, wherein said pair of guide pieces comprises a pair of guide arms projecting outwardly at opposite sides of said sensor.

14. The measuring system of claim 13, wherein said guide further has a base portion attached to said indicator device, said guide arms projecting outwardly from said base portion of said guide, said sensor being attached to said measuring device.

15. The measuring system of claim 12, wherein said pair of guide pieces comprises a pair of guide arms projecting outwardly from said measuring device so that a tip portion of each of said guide arms is located farther from said measuring device than said end portion of said sensor with respect to the projecting direction.

16. The measuring system of claim 15, wherein said guide further has a base portion attached to said indicator device, said guide arms projecting outwardly from said base portion of said guide, said sensor being attached to said measuring device.

17. The measuring system of claim 12, wherein said sensor projects from a front side of said measuring device, said measuring device being mounted to said indicator device, and said guide being attached to said indicator device so that said pair of guide pieces project from said front side of said measuring device at opposite sides of said sensor.

18. The measuring system of claim 12, wherein said sensor comprises a disposable sensor detachably connected to said measuring device.

19. The measuring system of claim 12, wherein said indicator device comprises an audio device for indicating the measured result generated by said measuring device by voice.

20. The measuring system of claim 12, wherein said guide is shaped and arranged as a clamp for fixing said measuring device to said indicator device.

21. The measuring system of claim 20, wherein said guide has a portion for contacting an end or a top surface of said measuring device so as to hold said measuring device against said indicator device.

22. The measuring system of claim 12, wherein said guide is retractably attached to said indicator device so as to be pulled from and stored in said indicator device.

23. The measuring system of claim 12, wherein said guide is removably mounted to said indicator device.

24. The measuring system as defined in claim 1, wherein said space between said pair of guide pieces is narrower at a base end of said guide closest to said measuring device than at a distal end of said guide farthest from said measuring device.

25. The measuring system as defined in claim 12, wherein said space between said pair of guide pieces is narrower at a base end of said guide closest to said measuring device than at a distal end of said guide farthest from said measuring device.

* * * * *